(12) United States Patent
Nelson

(10) Patent No.: US 12,310,632 B2
(45) Date of Patent: *May 27, 2025

(54) SPRING CAGE SPINAL FIXATION SYSTEMS

(71) Applicant: CTL Medical Corporation, Addison, TX (US)

(72) Inventor: Nathan Nelson, South Jordan, UT (US)

(73) Assignee: CTL Medical Corporation, Addison, TX (US)

( * ) Notice: Subject to any disclaimer, the term of this patent is extended or adjusted under 35 U.S.C. 154(b) by 171 days.

This patent is subject to a terminal disclaimer.

(21) Appl. No.: 18/208,691

(22) Filed: Jun. 12, 2023

(65) Prior Publication Data
US 2023/0320763 A1 Oct. 12, 2023

Related U.S. Application Data

(63) Continuation of application No. 17/517,145, filed on Nov. 2, 2021, now Pat. No. 11,672,569, which is a continuation of application No. 16/034,869, filed on Jul. 13, 2018, now Pat. No. 11,185,351, which is a continuation of application No. 15/069,663, filed on Mar. 14, 2016, now Pat. No. 10,052,136.

(60) Provisional application No. 62/132,237, filed on Mar. 12, 2015.

(51) Int. Cl.
*A61B 17/70* (2006.01)

(52) U.S. Cl.
CPC ...... *A61B 17/7037* (2013.01); *A61B 17/7001* (2013.01); *A61B 17/7032* (2013.01)

(58) Field of Classification Search
CPC ............ A61B 17/7001; A61B 17/7032; A61B 17/7037
See application file for complete search history.

(56) References Cited

U.S. PATENT DOCUMENTS

2013/0150852 A1* 6/2013 Shluzas .................. A61B 17/70
606/65
2015/0032162 A1* 1/2015 Biedermann ...... A61B 17/7035
606/278

* cited by examiner

*Primary Examiner* — Nicholas J Plionis
(74) *Attorney, Agent, or Firm* — BRAINSPARK ASSOCIATES, LLC

(57) ABSTRACT

Systems, methods and devices are disclosed for facilitating assembly and use of spinal fixation apparatus, including a helical cage structure for selective engaging and/or securing an engagement member or surgical screw in a spinal fixation system.

20 Claims, 14 Drawing Sheets

SPRING CAGE SPINAL FIXATION SYSTEMS

CROSS-REFERENCE TO RELATED APPLICATIONS

The present application is a continuation of U.S. patent application Ser. No. 17/517,145 entitled "SPRING CAGE PINAL FIXATION SYSTEMS," filed Nov. 2, 2021, which is a continuation of U.S. patent application Ser. No. 16/034,869 entitled "SPRING CAGE PINAL FIXATION SYSTEMS," filed Jul. 13, 2018 and issued as U.S. Pat. No. 11,185,351, which is a continuation of U.S. patent application Ser. No. 15/069,663 entitled "SPRING CAGE PINAL FIXATION SYSTEMS," filed Mar. 14, 2016 and issued as U.S. Pat. No. 10,052,136, which claims the benefit under 35 U.S.C. § 119(e) of U.S. Provisional Patent Application No. 62/132,237 entitled "SPRING CAGE PEDICLE SCREW SYSTEMS," filed Mar. 12, 2015. The disclosure and contents of these applications are incorporated herein by reference in their entireties.

SUMMARY

Disclosed herein are various embodiments of coupling mechanisms and elements for use in spinal fixation systems. For example, some embodiments may be particularly useful in connection with pedicle screw spinal fixation systems. In preferred embodiments, a connector body, such as a tulip, may be provided that is configured to receive a spring element, such as a spring cage structure, that may be configured to be received in the connector body and selectively flex to receive the head of an engagement member, such as a pedicle screw, to lock the engagement member in place within the connector body, In a more specific example of a spinal fixation system according to some embodiments, the system may comprise a connector body configured to be coupled with a spinal fixation rod, and an engagement member, such as a pedicle screw or another bone screw, comprising a head configured to be coupled with and received within the connector body, In some embodiments, the head may comprise an at least partially curved surface such as, in some embodiments, a frusto-spherical surface. The system may further comprise a spring cage structure configured to be coupled with the connector body. The spring cage structure may comprise a spring element configured to be positioned in a relaxed configuration and a flexed configuration. The spring may be configured to define an opening having a first size in the relaxed configuration and to expand such that the opening has a second, larger size in the flexed configuration, such that the opening can receive and engage the head of the engagement member.

In some embodiments, the spring may define an inner surface that expands, (in some embodiments, increases in radius) between the relaxed and flexed configurations to allow for receipt of the engagement member head. In some embodiments, at least a portion of the head of the engagement member may comprise an at least substantially spherical surface.

In some embodiments, the spring may comprise an inner surface configured to extend below a midpoint of a curvature of a sphere or other curved shape coincident with an at least substantially curved and/or spherical surface of the head such that the spring can engage both an upper portion of the head and a lower portion of the head in the relaxed configuration within the connector body. In some such embodiments, the spring may be further configured such that, in the flexed configuration, the inner surface Is configured to engage the upper portion of the head without simultaneously engaging the lower portion of the head.

Some embodiments may further comprise a saddle configured to be positioned within the connector body. The saddle may be configured to engage a spinal fixation rod. In some embodiments, the saddle may comprise an integral part of the spring cage structure. Alternatively, the saddle may be a separable element with respect to the spring cage structure. In some such embodiments, the saddle may be configured to be positioned adjacent to and/or engage the spring cage structure.

In some embodiments, the spring cage structure may comprise at least one helical cut extending along the spring. In some such embodiments, the spring cage structure may comprise a plurality of helical cuts extending along the spring.

In a specific example of a pedicle screw spinal fixation system according to some embodiments, the system may comprise a connector body configured to be coupled with a spinal fixation rod and a pedicle screw configured to be coupled with and received within the connector body. In some embodiments, the pedicle screw may comprise a head having an at least partially curved surface. In some such embodiments, the head may have an at least partially spherical surface, such as a frusto-spherical surface.

The system may further comprise a saddle configured to be positioned within the connector body and configured to engage a spinal fixation rod, along with a spring cage structure configured to be positioned within the connector body. As previously mentioned, in some embodiments, the saddle may comprise an integrated part of the spring cage structure, The spring cage structure may comprise a spring configured to be positioned in a relaxed configuration and a flexed configuration. The spring may be configured to define an at least partially curved (in some embodiments, at least partially spherical) inner surface for receiving the head of the pedicle screw. The at least partially curved/spherical inner surface may have a first radius in the relaxed configuration. The spring may be configured to expand such that the inner surface has a second, larger radius in the flexed configuration.

In some embodiments, the saddle and the spring cage structure may be distinct structures. In some such embodiments, the saddle may be configured to be coupled with an upper portion of the spring cage structure, such as by directly engaging and coupling the two elements together within the connector body for example.

In some embodiments, the saddle may comprise an upper portion configured to seat a spinal fixation rod and a lower portion comprising a protruding rim. In some such embodiments, the protruding rim may be configured to fit within the spring, such as within a flat portion of the at least partially curved/spherical inner surface of the spring. In some embodiments, the protruding rim may comprise an at least partially curved/spherical surface configured to engage the at least partially curved/spherical surface of the head.

In some embodiments, the upper portion of the saddle may be separated from the lower portion of the saddle by a flange extending about a periphery, or at least a portion of a periphery, of the saddle. In some such embodiments, the flange may be configured to engage a corresponding shelf formed within the spring cage structure.

The spring may comprise one or more helical cuts, which may extend between an upper portion of the spring and a lower portion of the spring. In some embodiments, the cut(s)

on one end of the spring may comprise open ends and the cut(s) on the opposite end may comprise closed ends.

The features, structures, steps, or characteristics disclosed herein in connection with one embodiment may be combined in any suitable manner in one or more alternative embodiments and/or implementations.

BRIEF DESCRIPTION OF THE DRAWINGS

The written disclosure herein describes illustrative embodiments that are nonlimiting and non-exhaustive. Reference is made to certain of such illustrative embodiments that are depicted in the figures, in which.

DETAILED DESCRIPTION

Figure 1:
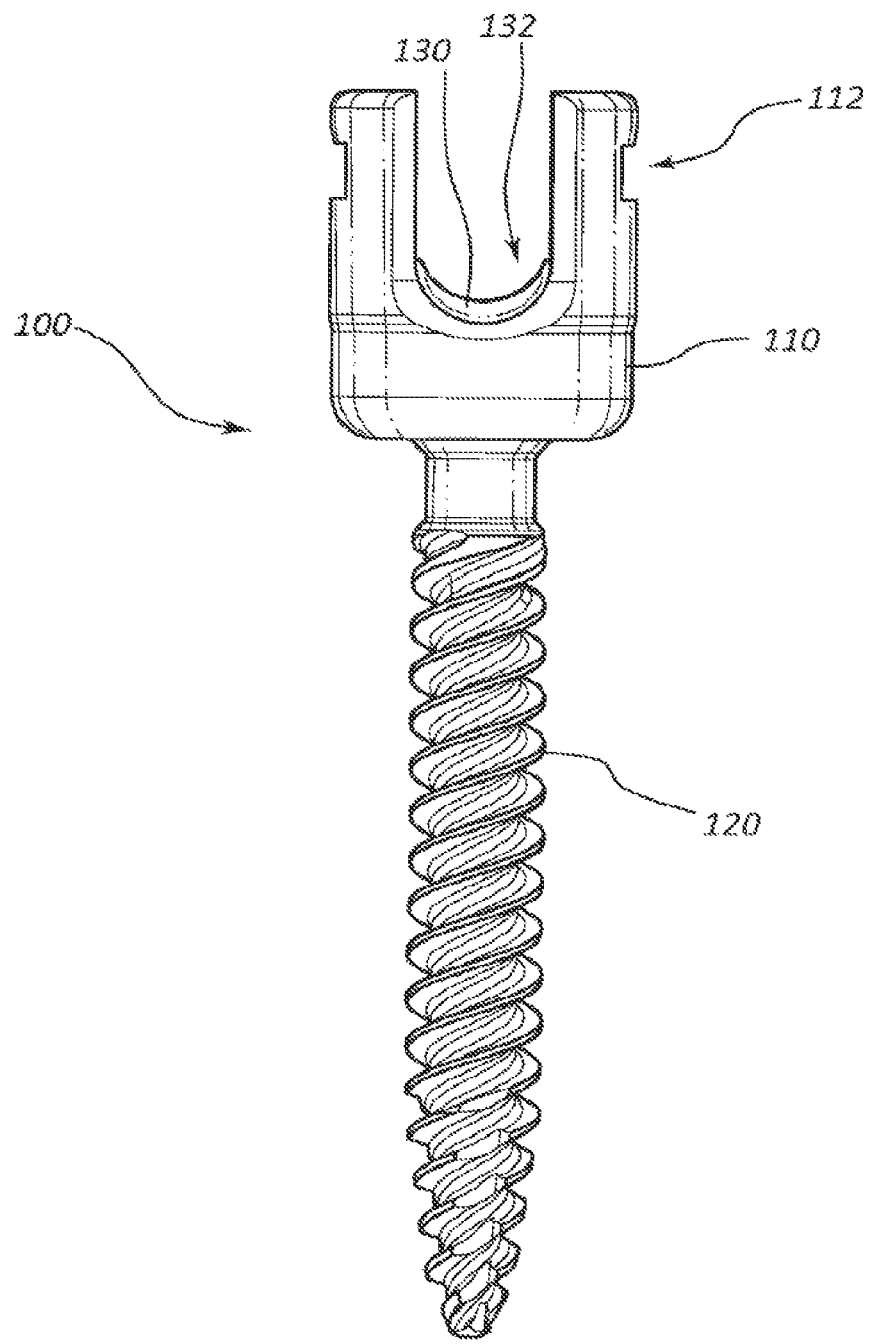
FIG. 1 is a perspective view of a spinal fixation system according to one embodiment.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases. well-known structures, materials, or operations are not shown or described in detail.

Various embodiments of apparatus, methods, and systems are disclosed herein that relate to spinal fixation system connectors. Some embodiments disclosed herein may, for example, be used to connect an engagement member, such as a pedicle screw, another bone screw, or hook, to a spinal fixation rod. Other embodiments may be used to couple a spinal fixation rod to another connector that may, in turn, be connected to a pedicle screw, another bone screw, or another such engagement member that may be engaged with a portion of a patient's vertebral column.

Embodiments disclosed herein may comprise a connector body, such as a tulip head connector body, that may comprise a slot at one end configured to allow a spinal fixation rod to extend therethrough at one end and may be configured to receive at least part of the head of a bone screw at the opposite end to facilitate coupling a spinal fixation rod to the bone screw. The connector body may also comprise two or more opposing sidewalls. Preferred embodiments, may comprise a spring cage structure positioned in a lower portion of the connector body such that the spring cage structure may directly engage at least a portion of the bone screw head to prevent the bone screw from backing out or otherwise being inadvertently removed from the connector body, and/or to lock the bone screw relative to the connector body in a desired angular and/or rotational position.

In some such embodiments, the spring cage structure may further comprise a saddle at a top end of the structure that may be configured to receive and engage a portion of a spinal fixation rod. In some embodiments, the spring cage structure may be designed with the saddle and the cage together as a unitary structure. Alternatively, the saddle may comprise a separate component configured to engage the spring cage structure, directly or indirectly, within the connector body. Still other embodiments, however, are contemplated in which the spring cage structure need not comprise a saddle component, nor be configured to engage a saddle component.

Additional details regarding certain preferred embodiments will now be described in greater detail with reference to the accompanying drawings. FIG. 1 depicts a perspective view of a spinal fixation system 100 incorporating an exemplary spring cage design according to one embodiment. Spinal fixation system 100 comprises a connector body 110, a bone screw 120, and a spring cage structure 130. As shown in this figure, spring cage structure 130 may be positioned within connector body 110 so as to define saddle 132, which may be configured to engage one side of a spinal fixation rod (not shown). Connector body 110 may have other features configured to engage other common components of spinal fixation systems, such as opposing slots 112, which may be configured to receive a cap or other similar structure configured to engage an opposite side of the spinal fixation rod relative to saddle 132. Similarly, internally grooves, slots, or threads 111 may be provided in order to receive a set screw or another fixation member.

Figure 2:
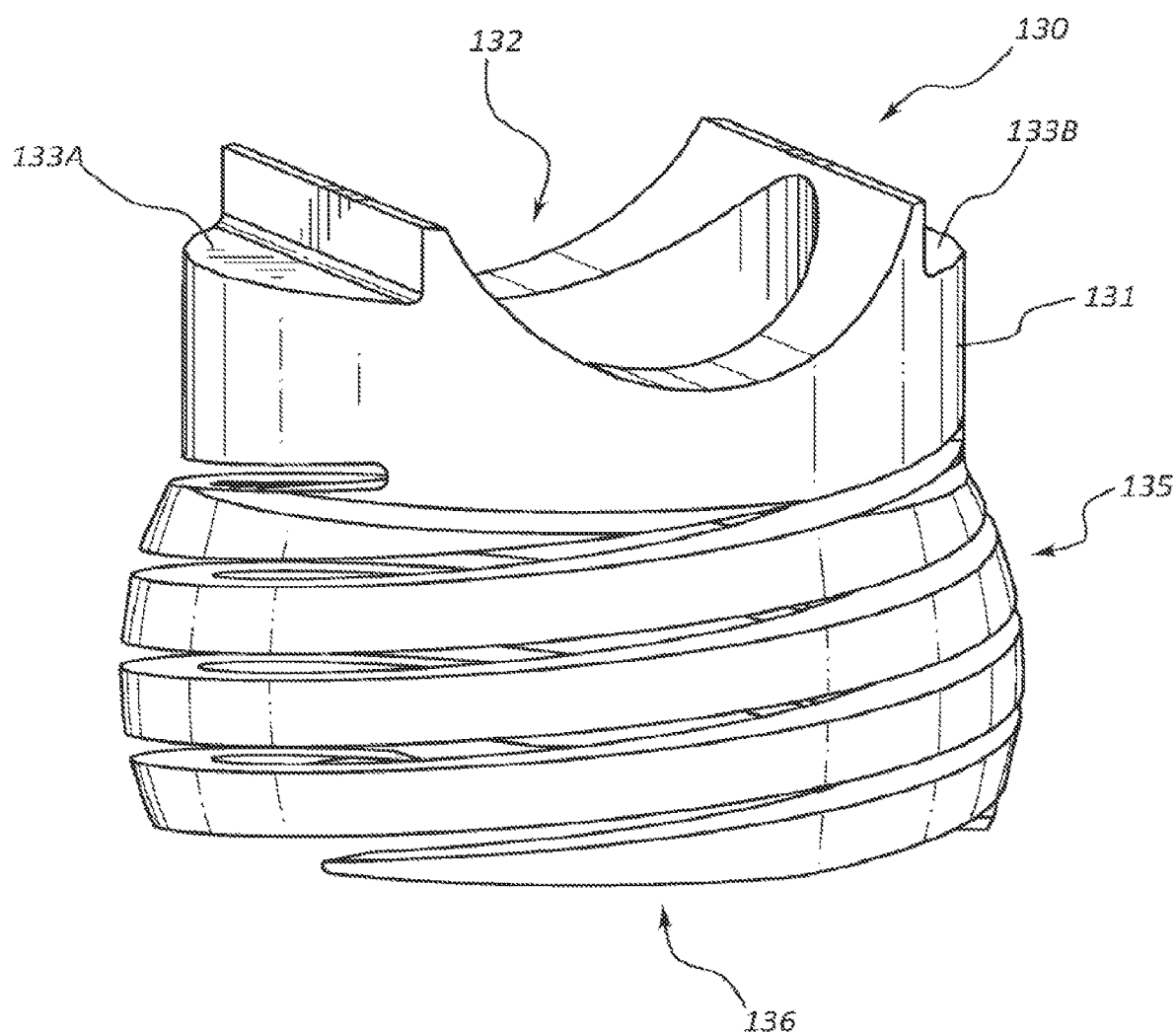
FIG. 2 is a perspective view of a spring cage structure for use in a spinal fixation system according to one embodiment.

Spring cage structure 130 is shown removed from connector body 110 in the perspective view of FIG. 2. As shown in this figure, spring cage structure 130 may comprise a spring 135 defining an opening 136 for receiving the head of a bone screw, such as a pedicle screw. In some embodiments, spring 135 may be formed to define an opening 136 configured to engage and match an outer surface of an at least substantially frusto-spherical surface. In some embodiments, as discussed below in connection with other figures, the inner surface of spring 135 defining opening 136 may be configured so as to extend below a midpoint of a curvature of a sphere coincident with the frusto-spherical surface so as to engage both upper and lower portions of an at least substantially frusto-spherical screw head in a relaxed configuration. In a flexed configuration, the inner surface of spring 135 defining opening 136 may be configured so as to only engage an upper portion of an at least substantially frusto-spherical screw head.

Spring cage structure 130 further comprises an upper portion 131 defining a saddle 132 for receiving a spinal fixation rod, as mentioned above. In order to facilitate desired coupling within a connector body, such as connector body 110, spring cage structure 130 further comprises opposing shelves 133A and 133B positioned on opposite ends of saddle 132. Shelves 133A and 133B may be configured to engage corresponding features within connector body 110, as depicted in other figures described below.

Figure 3:
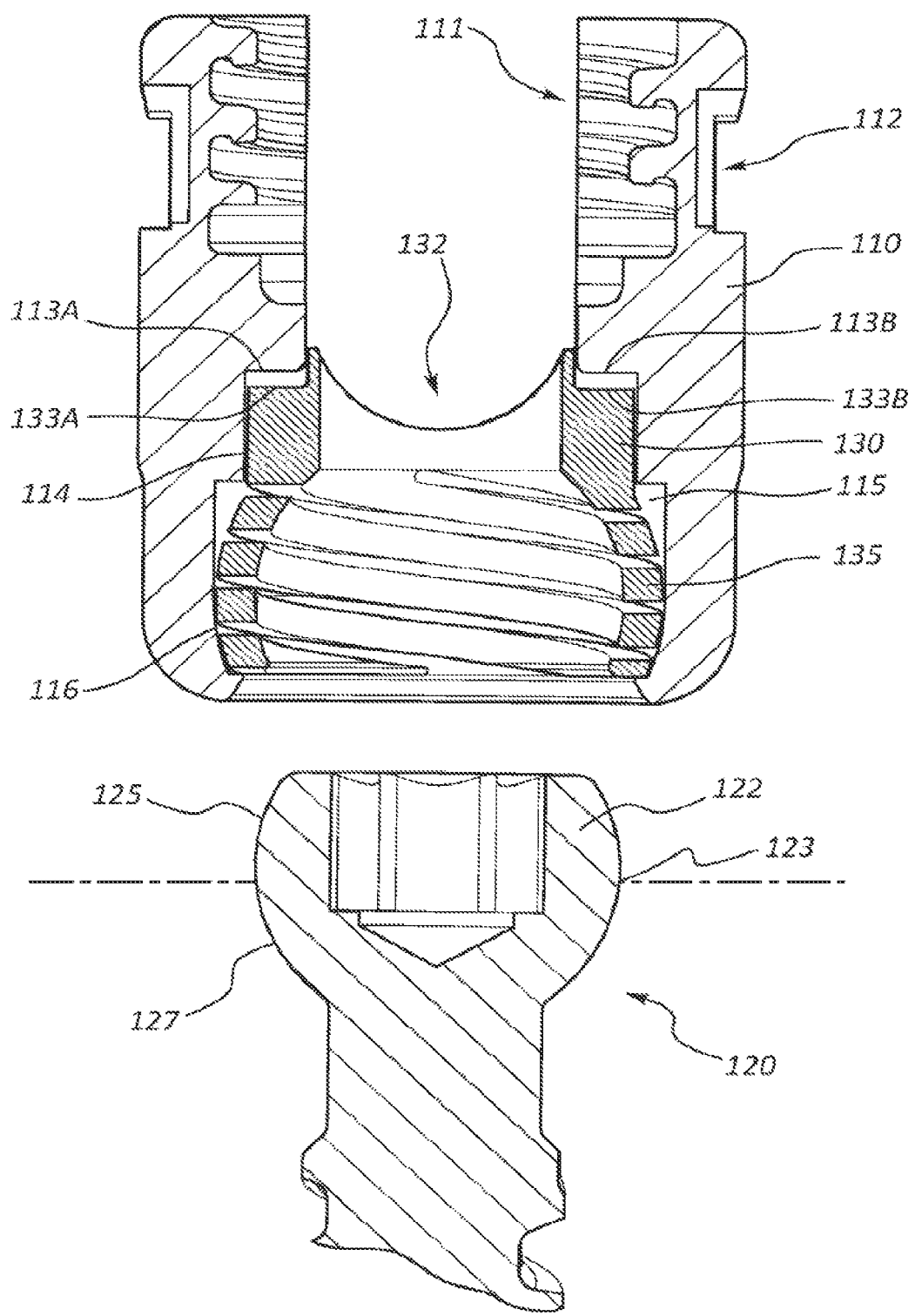
FIG. 3 is a cross-sectional view of a spinal fixation system according to one embodiment shown just prior to coupling a connector body of the system with a pedicle screw.

FIG. 3 is a cross-sectional view depicting a frusto-spherical head 122 of bone screw 120 positioned underneath connector body 110 with spring cage structure 130 positioned therein, as may represent a process of coupling connector body 110 with bone screw 120 during a surgical procedure. As shown in this figure, head 122 of bone screw 120 comprises a mid-point 123, which represents a boundary between an upper portion 125 or surface of head 122 and a lower portion 127 or surface of head 122.

As also shown in FIG. 3, connector body 110 defines a chamber 115 within which spring cage structure 130 may be positioned. Chamber 115 comprises opposing ledges 113A and 113B configured to engage opposing shelves 133A and 133B, respectively, of spring cage structure 130. Chamber 115 further comprises a first narrowed region 114 in which an exterior surface of an upper region of spring cage structure 130 may be positioned. Such upper region and first narrowed region 114 may comprise a cylindrical shape in some embodiments. Finally, a lower end of chamber 115 may comprise a spring-receiving portion 116. At least a portion of spring-receiving portion 116 may comprise a curvature and/or narrowing towards the distal end of chamber 115 configured to prevent spring cage structure 130 from being removed from chamber 115. An upper portion of spring-receiving portion 116 of chamber 115 may, however, like narrowed region 114, define a cylindrical shape if desired.

As further illustrated in FIG. 3, spring cage structure 130 may be configured such that, in a relaxed configuration/state, spring cage structure 130 defines an at least substantially frusto-spherical shape that extends below a mid-point 123 of a bone screw positioned therein so as to support at least a portion of a lower portion of the bone screw head, such as lower portion 127 of bone screw head 122, positioned therein. In this manner, a pedicle screw or other bone screw may be held within connector body 110 by spring cage structure 130, as explained in greater detail below.

Figure 4:
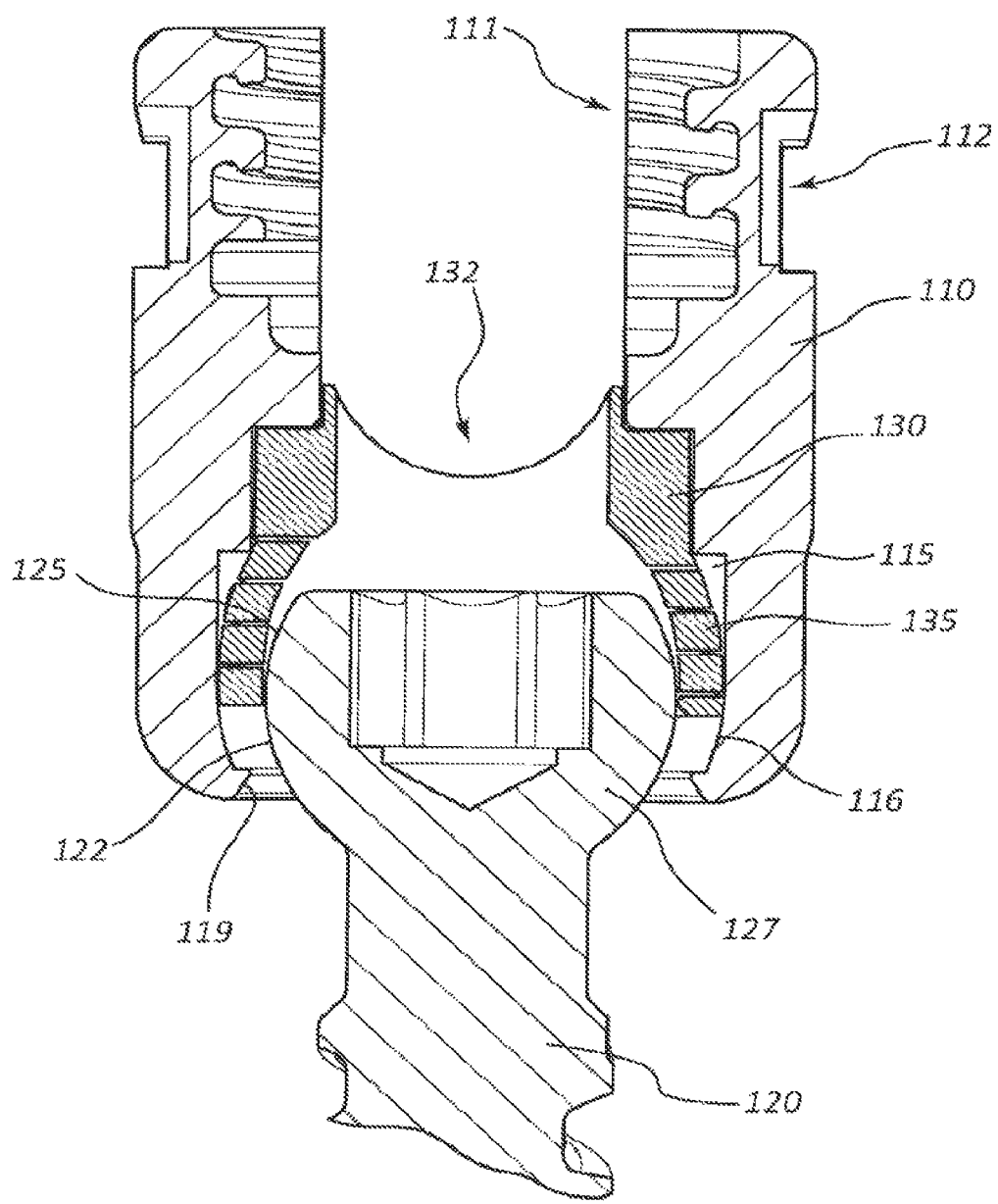
FIG. 4 is a cross-sectional view of the system of FIG. 3 shown with the head of the pedicle screw inserted into the spring cage structure and being forced up against the spring cage structure to expand the spring portion of the spring cage structure.

FIG. 4 is a cross-sectional view depicting frusto-spherical head 122 of bone screw 120 positioned within spring cage structure 130 of connector body 110. In this figure, head 122 of bone screw 120 has been pushed up against spring cage structure 130, which may expand the spring portion 135 of spring cage structure 130 to allow for head 122 to enter and be engaged by spring portion 135. In some embodiments, spring cage structure 130 may further be configured such that, upon pushing head 122 up against spring portion 135, spring portion 135 may be positioned at or above midpoint 123 to further facilitate a desired coupling between bone screw 120 and connector body 110. Spring portion 135 of spring cage structure 130 is shown in FIG. 4 in a flexed configuration.

In addition to or as an alternative to the features described above, spring cage structure 130 may be configured to operate in conjunction with chamber 115 of connector body 110 to engage bone screw head 122 by virtue of the shape of chamber 115 relative to spring cage structure 130. More particularly, as mentioned above, chamber 115 may comprise a spring-receiving portion 116 that narrows or otherwise has a narrowed region and/or diameter towards the distal end of chamber 115. In this manner, when spring cage structure 130 is forced upwards by bone screw head 122, spring cage structure 130 is moved up into a section of chamber 115 having a larger diameter, which allows the spring portion 135 of spring cage structure 130 to expand beyond the diameter of the bone screw head 122 and receive the bone screw head 122 therein. As soon as the spring portion 135 of spring cage structure 130 expands enough to receive bone screw head 122, it can relax and at least partially envelop the screw head 122.

Figure 5:
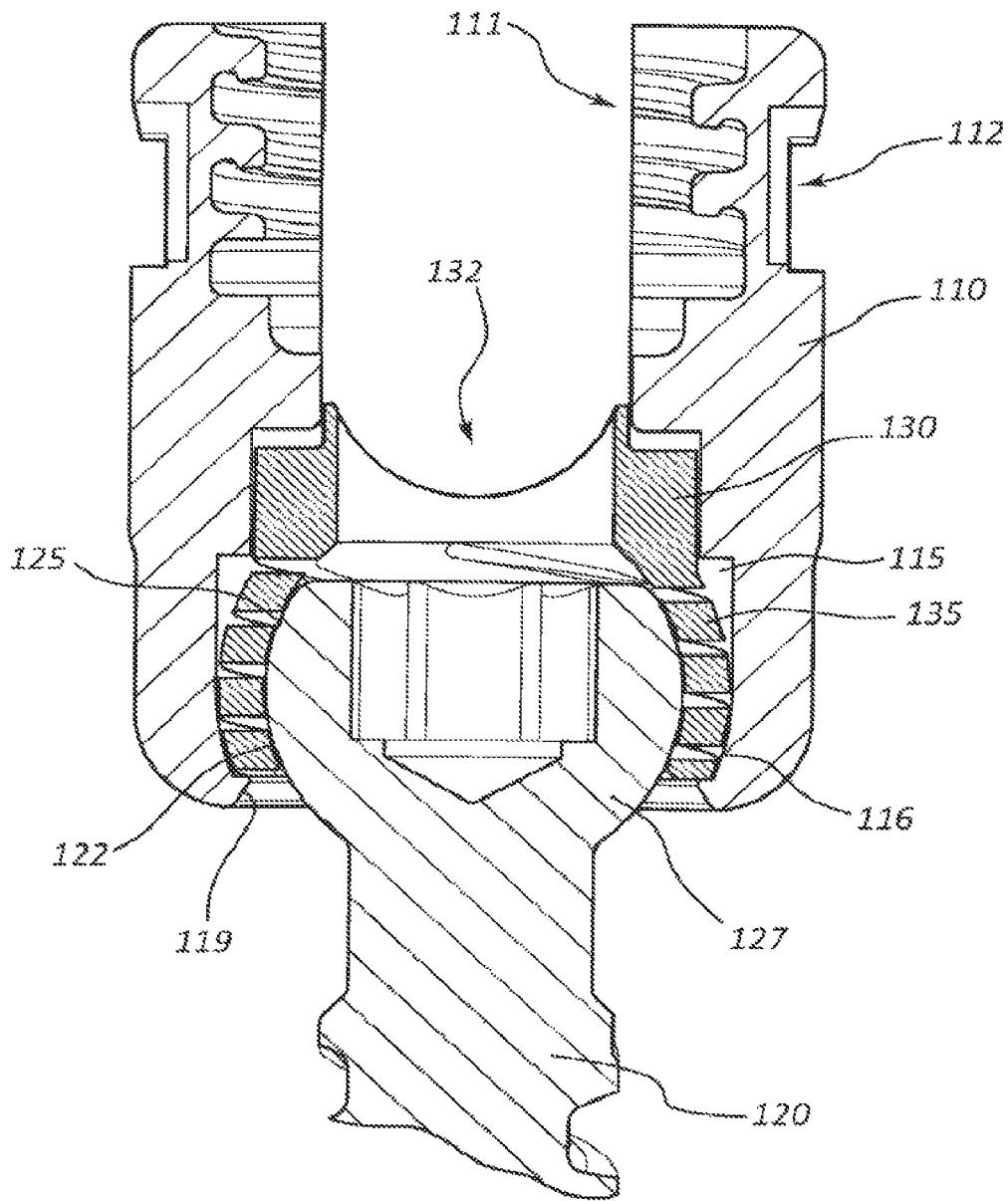
FIG. 5 is a cross-sectional view of the system of FIG. 4 shown after the force on the pedicle screw has been removed, thereby allowing the spring cage structure to relax and contract around the head of the pedicle screw.

Upon releasing the upward force on bone screw 120, spring portion 135 of spring cage structure 130 is free to return to its relaxed configuration, as shown in FIG. 5. As also shown in FIG. 5, in its relaxed configuration, spring portion 135 of spring cage structure 130 extends about a greater portion of the head 122 of bone screw 120. However, in some embodiments, as alluded to above, spring portion 135 of spring cage structure 130 may relax and at least partially envelop bone screw head 122 without requiring the upward force on bone screw 120 to be released.

Since stretching of spring portion 135 causes the diameter of the head receiving seat of this spring to contract, any forces tending to pull bone screw 120 out of connector body 110 will generate a contracting force on bone screw head 122, which will serve to prevent bone screw head 122 from being withdrawn from chamber 115 and thereby decoupled from connector body 110.

In some embodiments, the interaction between bone screw head 122, chamber 115, and spring portion 135 of spring cage structure 130, may be sufficient alone (i.e., without regard to the ability of spring portion 135 to contract as it is stretched) to keep the full assembly in place. More particularly, once bone screw head 122 has been captured within spring portion 135, the narrower region towards the bottom of spring-receiving portion 116 of chamber 115 may serve to prevent, or at least inhibit, spring portion 135 from opening to a sufficient degree to allow bone screw head 122 to back out.

In some embodiments, connector body 110 may comprise one or more features designed to cooperate with spring cage structure 130 and/or further prevent undesired decoupling of a bone screw head from a connector body. For example, chamber 115 of connector body 110 may comprise a lip 119 extending about a periphery of a lower opening of chamber 115. Lip 119 may serve to restrain spring cage structure 130 from being removed from chamber 115, and thereby further restrain bone screw head 122 within spring portion 135 of spring cage structure 130. However, other embodiments are contemplated in which lip 119 may be omitted. For example, certain chamber shapes, spring shapes, and materials may be used that may render this feature unnecessary for certain implementations.

It can also be seen in FIG. 5 that, in some embodiments, the dimensions of chamber 115 and spring cage structure 130 may be designed such that a small gap 117 may be formed in between upper portion 131 of spring cage structure 130 (more particularly, opposing shelves 133A and 133B) and an upper portion of connector body 110 defining chamber 115 (more particularly, ledges 113A and 113B). Gap 117 may facilitate desired coupling between bone screw head 122 and spring cage structure 130 and/or between a set screw or other fixation member and a spinal fixation rod (not shown).

Spinal fixation system 100 may be configured to accommodate a pedicle screw or other bone screw 120 at any of a variety of angles with respect to connector body 110. In some embodiments, connector body 110 and/or spring cage structure 130 may be configured such that a bone screw 120 may be repositioned at any such angle until a set screw or other fixation member is used to drive a spinal fixation rod into saddle 132, which may then result in locking of the bone screw 120 at a particular angle with respect to connector body 110.

Figure 6:
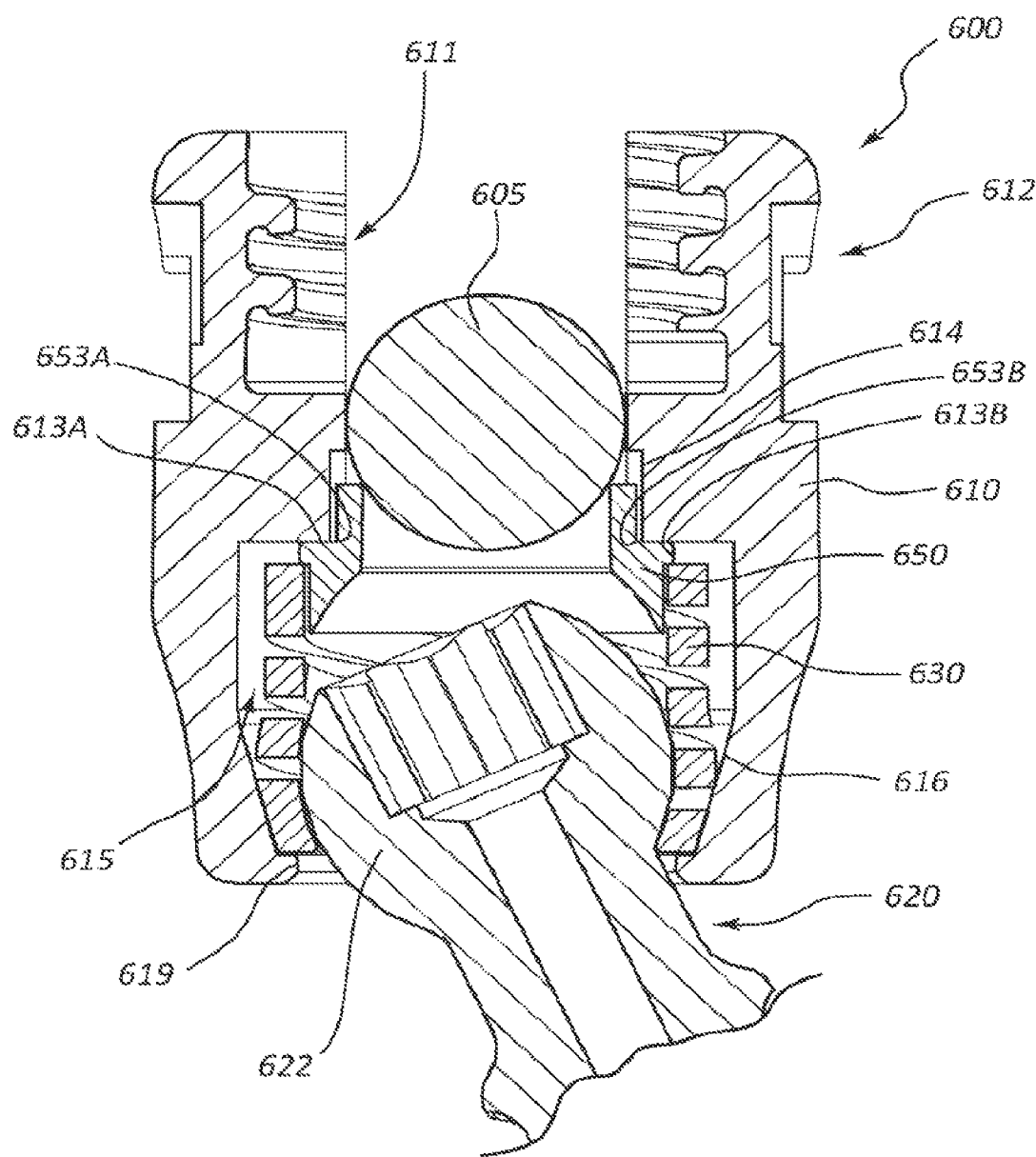
FIG. 6 is a cross-sectional view of a spinal fixation system according to another embodiment shown after coupling a connector body of the system with a pedicle screw.

FIG. 6 is a cross-sectional view of a spinal fixation system 600 according to another embodiment. Spinal fixation system 600 comprises a connector body 610, a bone/pedicle screw 620, a spring cage structure 630, and a saddle 650, Unlike spinal fixation system 100, system 600 therefore includes a spring cage structure 630 that does not comprise a saddle. Instead, saddle 650 is a separate element that is coupleable within connector body 610 to spring cage structure 630, as described in greater detail below.

Spring cage structure 630 may be positioned within a chamber 615 of connector body 610 and saddle 650 may be positioned adjacent spring cage structure 630 within chamber 615. More particularly, spring cage structure 630 may be positioned in a lower, spring-receiving portion 616 portion of chamber 615 and saddle 650 may be positioned within an upper, narrowed region 614 of chamber 615. One or more portions of chamber 615, such as narrowed region 614 and/or at least a portion of spring-receiving portion 616, may comprise a cylindrical shape in some embodiments.

Chamber 615 comprises opposing ledges 613A and 613B configured to engage opposing shelves 653A and 653B, respectively, of saddle 650. Thus, in some embodiments, at least a portion of a lower surface of one or both of shelves 653A/653B may engage a top surface of spring cage structure 630. However, alternative embodiments are contemplated in which grooves, slots, shelves or the like, may be formed in spring cage structure 630 to further facilitate desired engagement between spring cage structure 630 and saddle 650. In still other embodiments, shelves 653A/653B, or another portion of saddle 650, may instead be configured to be positioned adjacent to, rather than on top of, a corresponding feature of spring cage structure 630.

At least a portion of spring-receiving portion 616 may comprise a curvature and/or narrowing towards the distal end of chamber 615 configured to prevent spring cage structure 630 from being removed from chamber 615. However, unlike chamber 115, chamber 615 comprises a narrowed distal end that defines a conical surface rather than a curved surface. A lip 619 may be formed around the periphery of an engagement member-receiving opening to chamber 615 to further retain bone screw 620 and/or spring cage structure 630.

Like connector body 110, connector body 610 may further comprise opposing slots 612, which may be configured to receive a cap or other similar structure configured to engage an opposite side of a spinal fixation rod 605 relative to saddle 650. Similarly, internally grooves, slots, or threads 611 may be provided in order to receive a set screw or another fixation member.

As with previously-described embodiments, spring cage structure 630 may be configured such that, in a relaxed configuration/state, spring cage structure 630 defines an at least partially curved inner surface, such as an at least substantially frusto-spherical inner surface, that extends below a mid-point of a bone screw or other fastener or engagement member positioned therein so as to support at least a portion of a lower portion of a bone screw head 622 positioned therein. In this manner, a pedicle screw 620 or other bone screw may be held within connector body 610 by spring cage structure 630.

Although FIG. 6 depicts system 600 in a relaxed configuration after coupling bone screw 620 with spring cage structure 630, it should be understood that this embodiment may operate in a similar manner to that of system 100. Thus, bone screw 620 may be coupled with spring cage structure 630 by pushing head 622 of bone screw 620 against spring cage structure 630, thereby expanding the spring portion of spring cage structure 630 to a flexed configuration in which the inner surface of spring cage structure is larger (in some embodiments, this inner surface may have a larger diameter) to allow for head 622 to enter and be engaged by spring cage structure 630. In some embodiments, spring cage structure 630 may further be configured such that, upon pushing head 622 up against spring cage structure 630, the spring portion of spring cage structure 630 may be positioned at or above a midpoint between the bottom and top of head 622 to further facilitate a desired coupling between bone screw 620 and connector body 610.

Upon releasing the upward force on bone screw 620, spring cage structure 630 may then return to its relaxed configuration, as depicted in FIG. 6 (or at least a more relaxed configuration than its fully flexed configuration). As also shown in FIG. 6, in its relaxed configuration, spring cage structure 630 extends about a greater portion of the head 622 of bone screw 620 than in its flexed configuration.

In some embodiments, spring cage structure 630 may be configured to operate in conjunction with chamber 615 of connector body 610 to engage bone screw head 622 by virtue of the shape of chamber 615 relative to spring cage structure 630. For example, in some embodiments, chamber connector body 610 and/or spring cage structure 630 may be configured such that, when spring cage structure 630 is forced upwards by bone screw head 622, spring cage structure 630 is moved up into a section of chamber 615 having a larger size and/or diameter, which may allow spring cage structure 630 to expand beyond the diameter of the bone screw head 622 and receive the bone screw head 622 therein. As soon as spring cage structure 630 has expanded sufficiently to receive bone screw head 622, it can relax and at least partially envelop the screw head 622.

As previously discussed in connection with FIG. 5, in some embodiments, the dimensions of chamber 615 and/or spring cage structure 630 may be designed such that a small gap may be formed in between an upper portion of spring cage structure 630 and an upper portion of connector body 610 defining chamber 615 to facilitate desired coupling between bone screw head 622 and spring cage structure 630 and/or between a set screw or other fixation member and a spinal fixation rod 605.

In addition, like other embodiments described above, spinal fixation system 600 may be configured to accommodate a pedicle screw or other bone screw 620 at any of a variety of angles with respect to connector body 610. In some such embodiments, connector body 610 and/or spring cage structure 630 may be configured such that a bone screw 620 may be repositioned at any such angle until a set screw or other fixation member is used to drive a spinal fixation rod into saddle 650, which may, in turn, contact bone screw head 622 and thereby result in locking of the bone screw 620 at a particular angle with respect to connector body 610.

Since stretching of the spring of spring cage structure 630 causes the size and/or diameter of the head-receiving seat/inner surface of this spring to contract, any forces tending to pull bone screw 620 out of connector body 610 will generate a contracting force on bone screw head 622, which will serve to prevent bone screw head 622 from being withdrawn from chamber 615 and thereby decoupled from connector body 610. In some embodiments, providing a tight fit of spring cage structure 630 within chamber 615 may further provide this desired effect by wedging spring cage structure 630 against the structure of connector body 610 defining chamber 615.

Figure 7A:
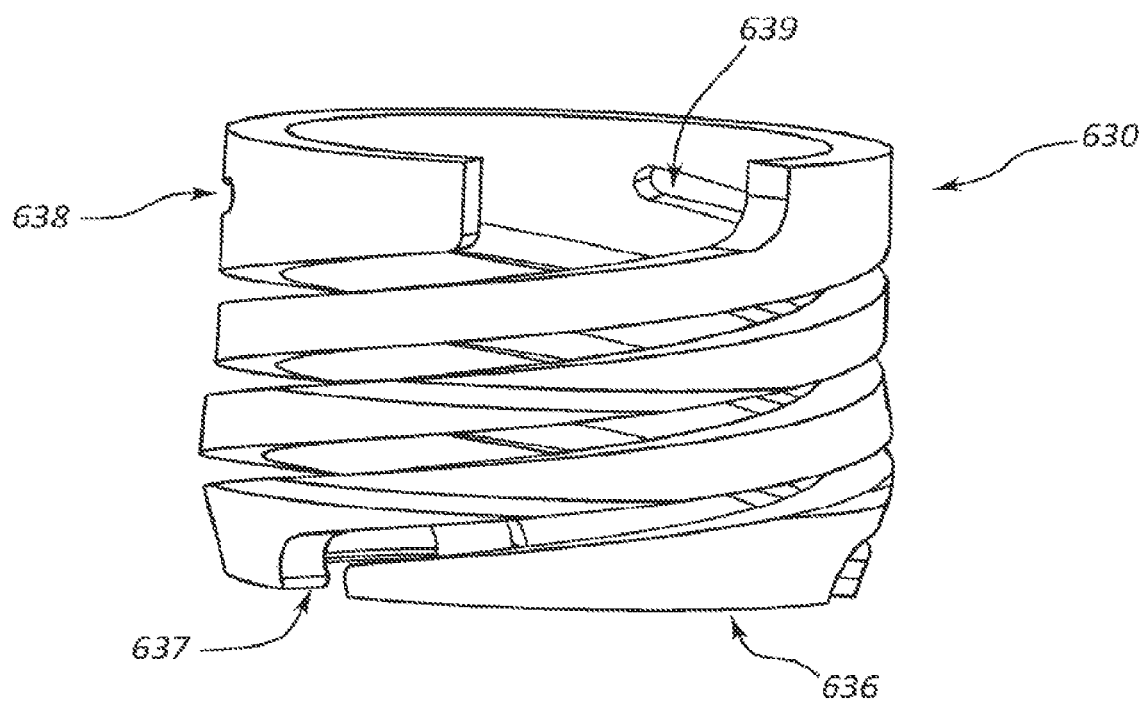
FIG. 7A is a side perspective view of a spring cage structure of the spinal fixation system depicted in FIG. 6.
Figure 7B:
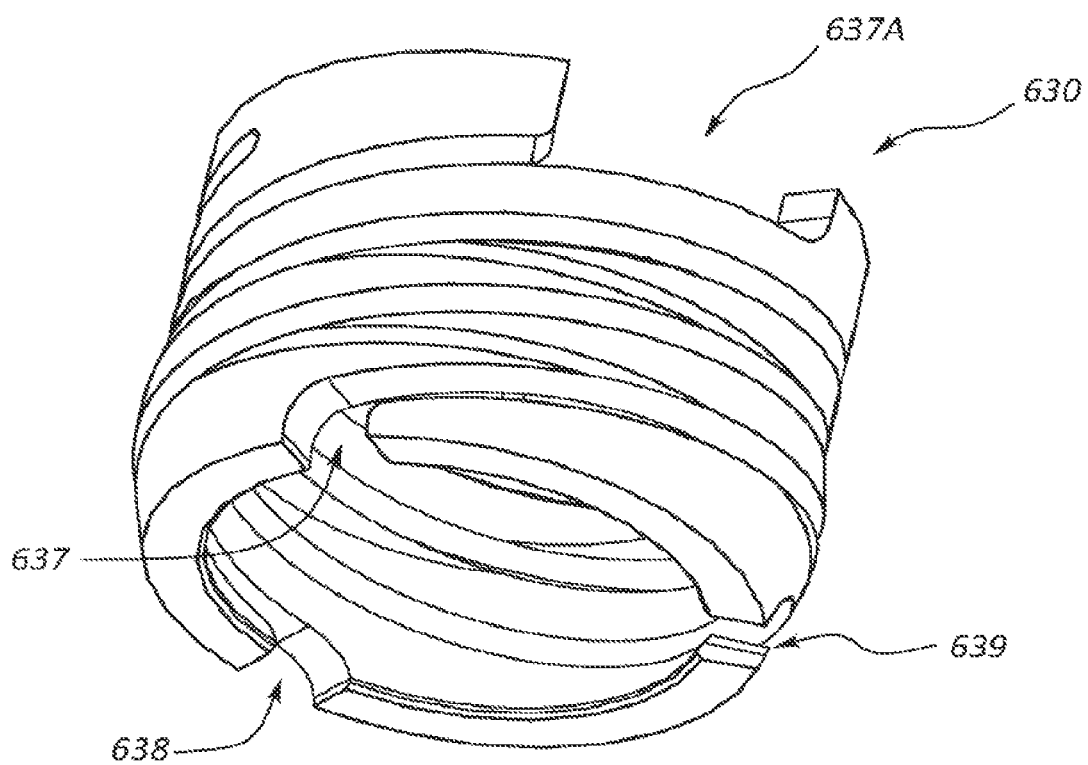
FIG. 7B is a lower perspective view of the spring cage structure of FIG. 7A.

Spring cage structure 630 Is shown removed from connector body 610 in the perspective views of FIGS. 7A and 7B. As shown in these figures, spring cage structure 630 defines an opening 636 for receiving the head of a bone screw, such as a pedicle screw. In some embodiments, spring cage structure 630 may be formed to define an opening 636 leading to an inner surface configured to engage and match an outer surface of an at least partially curved head of a bone screw or other engagement member, In some such embodiments, this inner surface may comprise a substantially frusto-spherical surface matching a corresponding frusto-spherical outer surface of a bone screw head, such as bone screw head 622.

Spring cage structure 630 further comprises three separate helical cuts extending between opposing surfaces of spring cage structure 630. More particularly, a first helical cut 637 extends from an opening in a bottom surface of spring cage structure 630 to an opening in a top surface of spring cage structure 630. Second and third helical cuts 638 and 639, respectively, may extend from respective openings in a bottom surface of spring cage structure 630 to respective terminal ends adjacent to a top surface of spring cage structure 630. In some embodiments, one or more (in some embodiments, all) of the openings may be formed to curve from the helical curve defining the cut to extend at least substantially parallel to the axis of the spring cage structure 630, as shown in FIGS. 7A and 7B. Moreover, in the depicted embodiment, the top opening of helical cut 637 may comprise a gap 637A configured to allow for a desired amount of compression to allow spring cage structure 630 to be positioned in chamber 615.

In some embodiments, each of the plurality of helical cuts (embodiments are contemplated having fewer or greater than three) is evenly spaced about a perimeter of spring cage structure 630. Thus, in embodiments comprising three helical cuts, a first of the cuts may begin at a first angle when viewed from a top plan view, a second of the cuts may begin at an angle spaced from the first angle by about 120 degrees, and a third of the cuts may begin at an angle spaced from the first angle by about 240 degrees (and spaced from the second angle by about 120 degrees).

In addition, in some embodiments, a lower portion of the spring cage structure may comprise a tapered or curved surface configured to match, or at least substantially match, a corresponding surface of an interior surface of the connector body, such as chamber 615 of connector body 610. For example, in the embodiment depicted in FIGS. 6 and 7A/7B, the exterior surface near the bottom of spring cage structure 630 tapers and forms a conical shape that at least substantially matches the tapered, conical shape near the bottom of chamber 615.

Figure 8A:
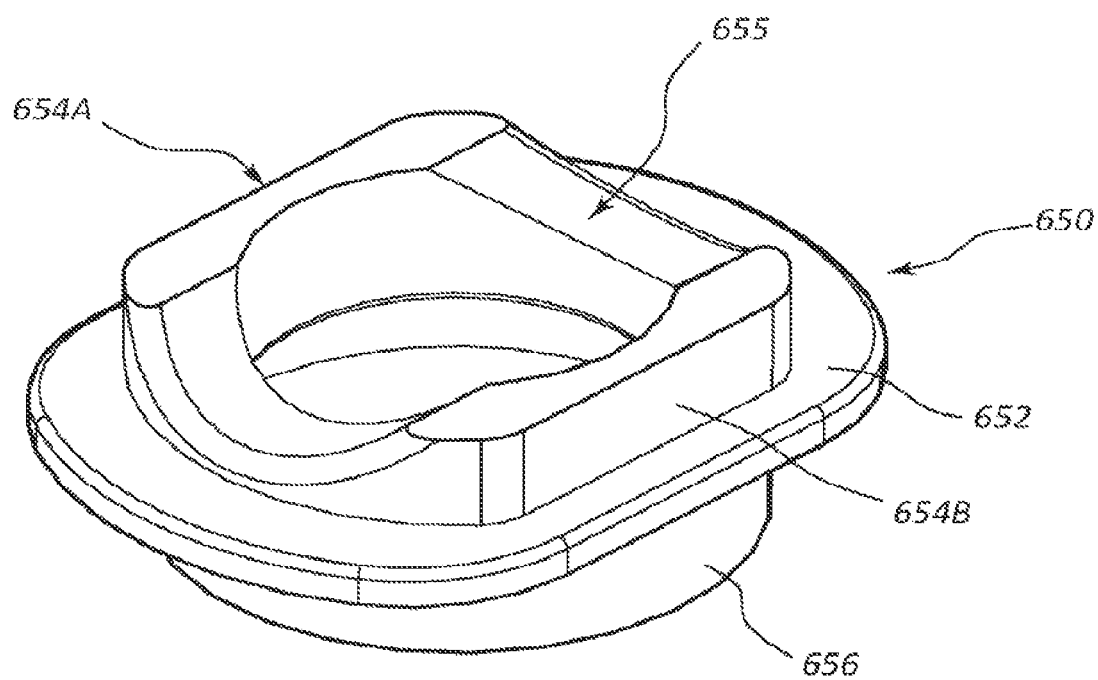
FIG. 8A is a side perspective view of a saddle element of the spinal fixation system depicted in FIG. 6.
Figure 8B:
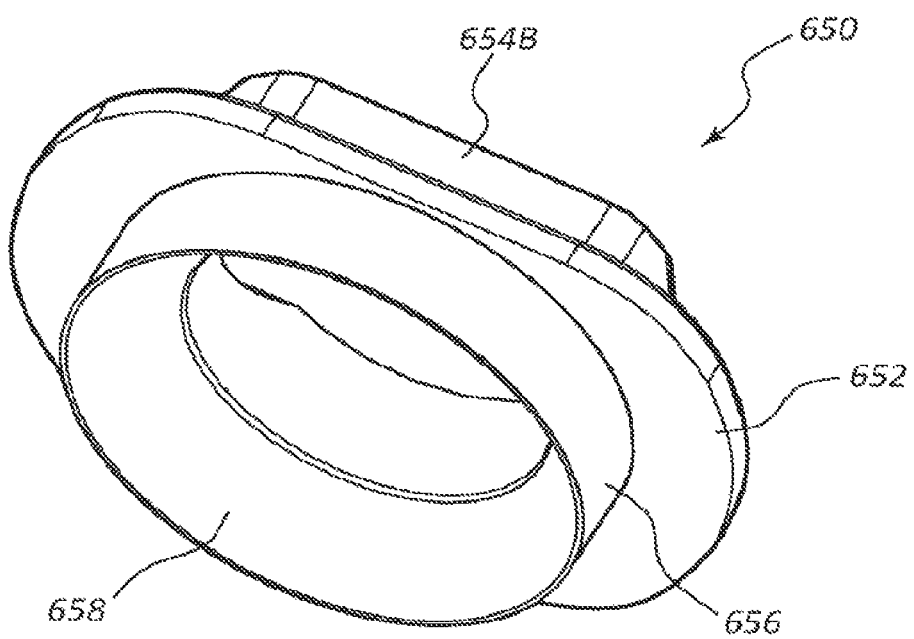
FIG. 8B is a lower perspective view of the saddle element of FIG. 8A.

FIGS. 8A and 8B are perspective views of saddle 650 shown removed from connector body 610. As depicted in these figures, saddle 650 may comprise an upper portion comprising a seat 655 configured to receive and seat a spinal fixation rod 605. The upper portion of saddle 650 may, in some embodiments, comprise flattened opposing sidewalls 654A and 654B, In some embodiments, a first dimension extending between sidewalls 654A and 654B may be smaller than a second dimension perpendicular to the first dimension. One or both of these features may allow the saddle 650 to be inserted from the top of connector body 610 with one of the opposing sidewalls 654A and 654B facing down towards chamber 615. The saddle 650 may then be rotated by ninety degrees to position saddle 650 within connector body 610 in the position shown in FIG. 6.

Saddle 650 may further comprise a lower portion comprising a protruding rim 656. Protruding rim 656 may comprise an inner surface 658 configured to receive and engage at least a portion of a bone screw head, such as bone screw head 622. In some embodiments, surface 658 may comprise a curved surface, or an at least partially curved surface, that is configured to at least substantially match and/or mate with a corresponding surface of bone screw head 622. In the depicted embodiment, protruding rim 656 comprises an at least partially spherical surface configured to engage and/or at least partially mate with the at least partially spherical surface of bone screw head 622.

In the depicted embodiment, protruding rim 656 may be configured to extend and/or fit within spring cage structure 630, Thus, in some such embodiments, protruding rim 656 may be configured to fit within and be positioned adjacent to an inner surface of spring cage structure 630, as depicted in FIG. 6.

In the depicted embodiment, the upper portion of saddle 650 is separated from the lower portion of saddle 650 by a flange 652 extending about a periphery of saddle 650. Flange 652 may be configured to engage a corresponding shelf or other similar feature formed within spring cage structure 630. Alternatively, flange 652 may simply rest on an upper surface of spring cage structure 630 or may be positioned within a shelf, recess, or other such engagement feature within connector body 610.

Figure 9:
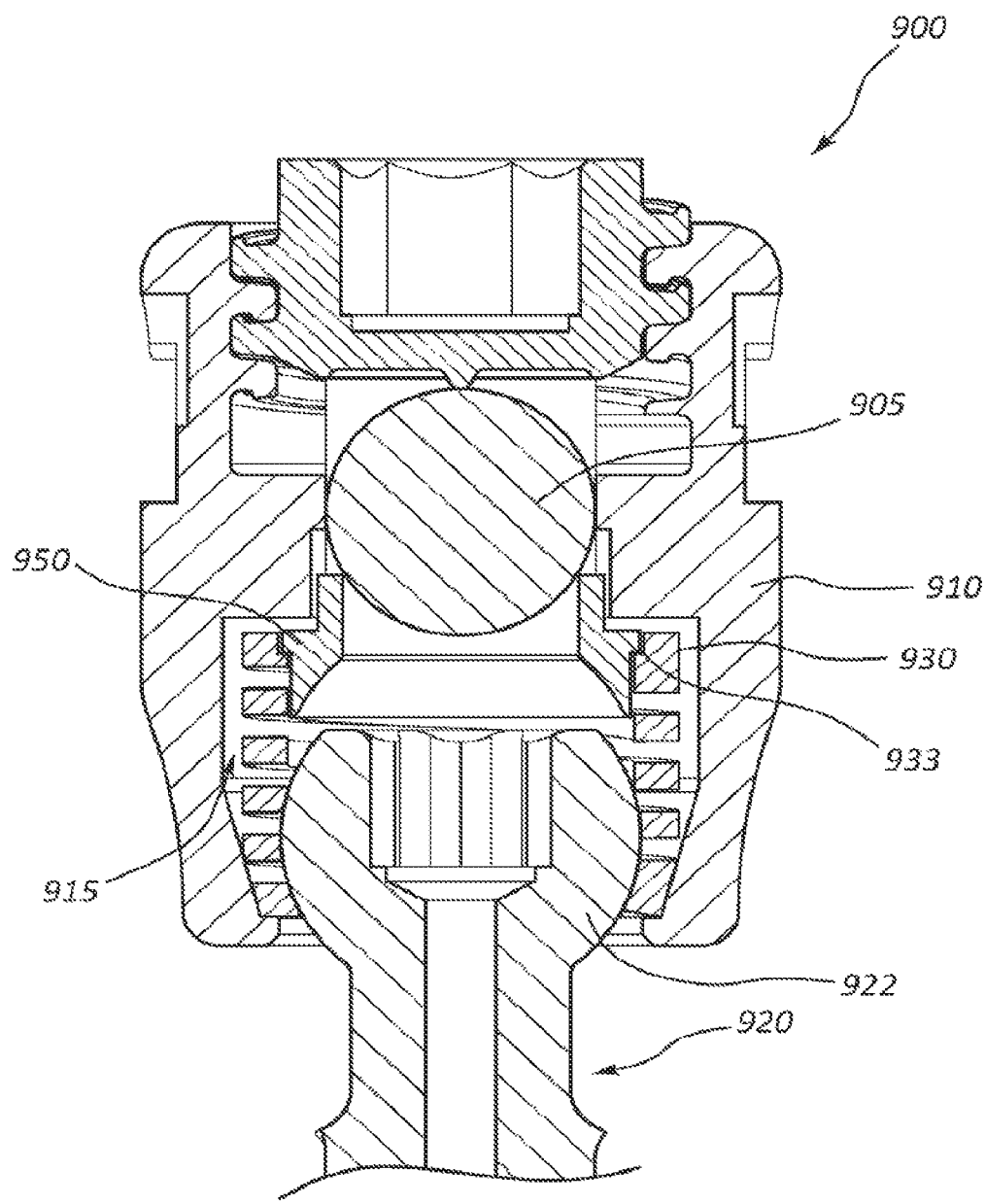
FIG. 9 is a cross-sectional view of a spinal fixation system according to yet another embodiment shown after coupling a connector body of the system with a pedicle screw.
Figure 10:
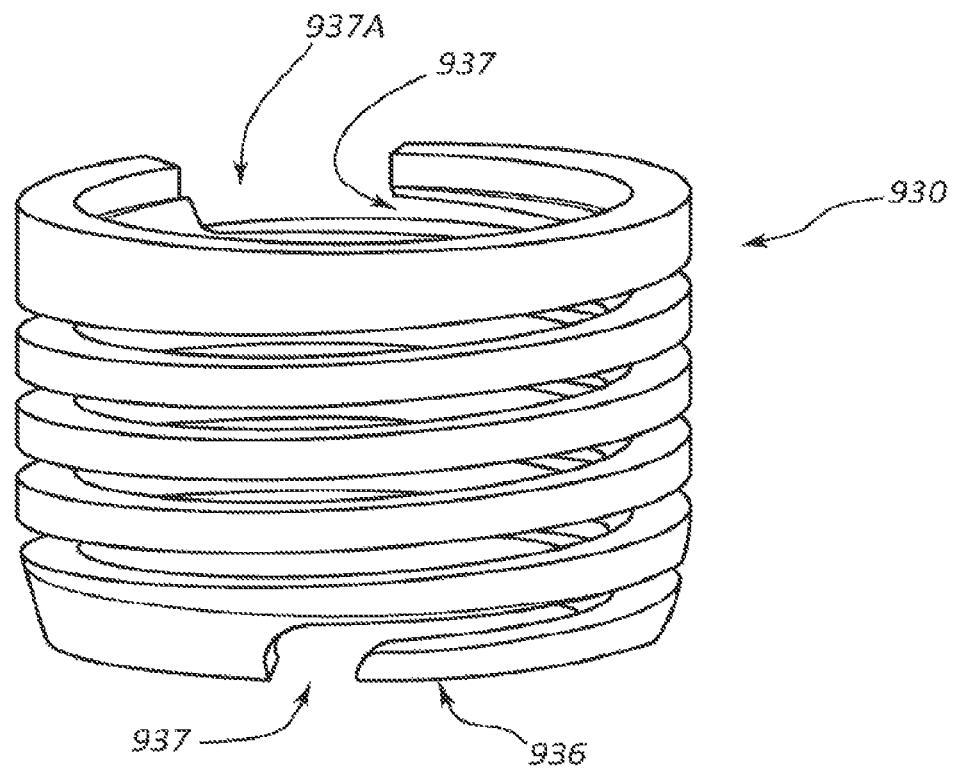
FIG. 10 is a perspective view of a spring cage structure of the spinal fixation system depicted in FIG. 9.

FIG. 9 is a cross-sectional view of a spinal fixation system 900 according to yet another embodiment shown after coupling a connector body 910 of the system 900 with the head 922 a pedicle screw 920 and with a spinal fixation rod 905. System 900 is similar to those previously described with a few exceptions. For example, spring cage structure 930 of system 900 comprises a single helical cut 937, as best shown in FIG. 10. Helical cut 937 extends all the way between opposing openings in opposing surfaces of spring cage structure 930 to allow spring cage structure 930 to, as previously described, flex to receive a bone screw head 922 and then clamp down on bone screw head 922 to retain head 922 within a chamber 915 of connector body 910. Like spring cage structure 630, a gap 937A is formed in the top opening of spring cage structure 930 adjacent helical cut 937 to allow for a desired amount of expansion/compression. The size of gap 937A may be adjusted as desired in accordance with the dimensions/specifications of various elements within system 900.

Figure 11:
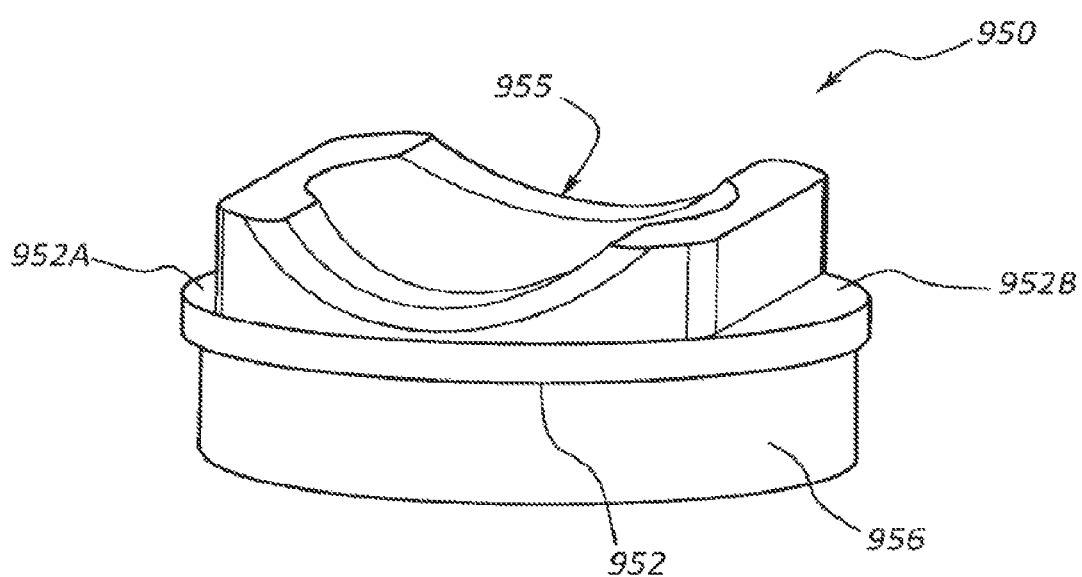
FIG. 11 is a perspective view of a saddle element of the spinal fixation system depicted in FIG. 9.

In addition, as best seen in FIG. 11, saddle 950 of spinal fixation system 900 differs from saddle 650 in several respects. For example, saddle 950 comprises an upper portion comprising a seat 955 configured to receive and seat a spinal fixation rod 905 and a lower portion comprising a protruding rim 956, as previously described in connection with saddle 650. However, the upper portion of saddle 950 is separated from the lower portion of saddle 950 by a flange 952 that only extends about a portion of the periphery of saddle 950. More particularly, flange 952 is made up of a first flange section 952A positioned on a first side of saddle 950 and a second flange section 952B positioned on a second side of saddle 950 opposite from the first side when viewed from the top of saddle 950. However, lower portions of flange 952 may extend beyond flange sections 952A and 952B around the entire periphery of saddle 950 to form a ledge for engagement with a corresponding feature, such as a shelf, formed within connector body 910 and/or spring cage structure 930. More particularly, in the depicted embodiment, flange 952 may be configured to engage shelf 933 that may be formed in at least a portion of spring cage structure 930. In some embodiments, shelf 933 may be configured to extend 360 degrees around spring cage structure 930.

As described in connection with saddle 650, protruding rim 956 may comprise an inner surface (not shown) configured to receive and engage at least a portion of a bone screw head, such as bone screw head 922. This inner surface may comprise a curved surface, or an at least partially curved surface, that is configured to at least substantially match and/or mate with a corresponding surface of bone screw head 922. Further, protruding rim 956 may be configured to extend and/or fit within an interior surface of spring cage structure 930, as depicted in FIG. 9. In addition, as described in connection with spring cage structure 630, spring cage structure 930 may have an exterior surface near the lower end of the spring cage structure 930 that is tapered or curved to match, or at least substantially match, a corresponding surface of an interior surface of connector body 910, such as chamber 915 of connector body 910.

Figure 12:
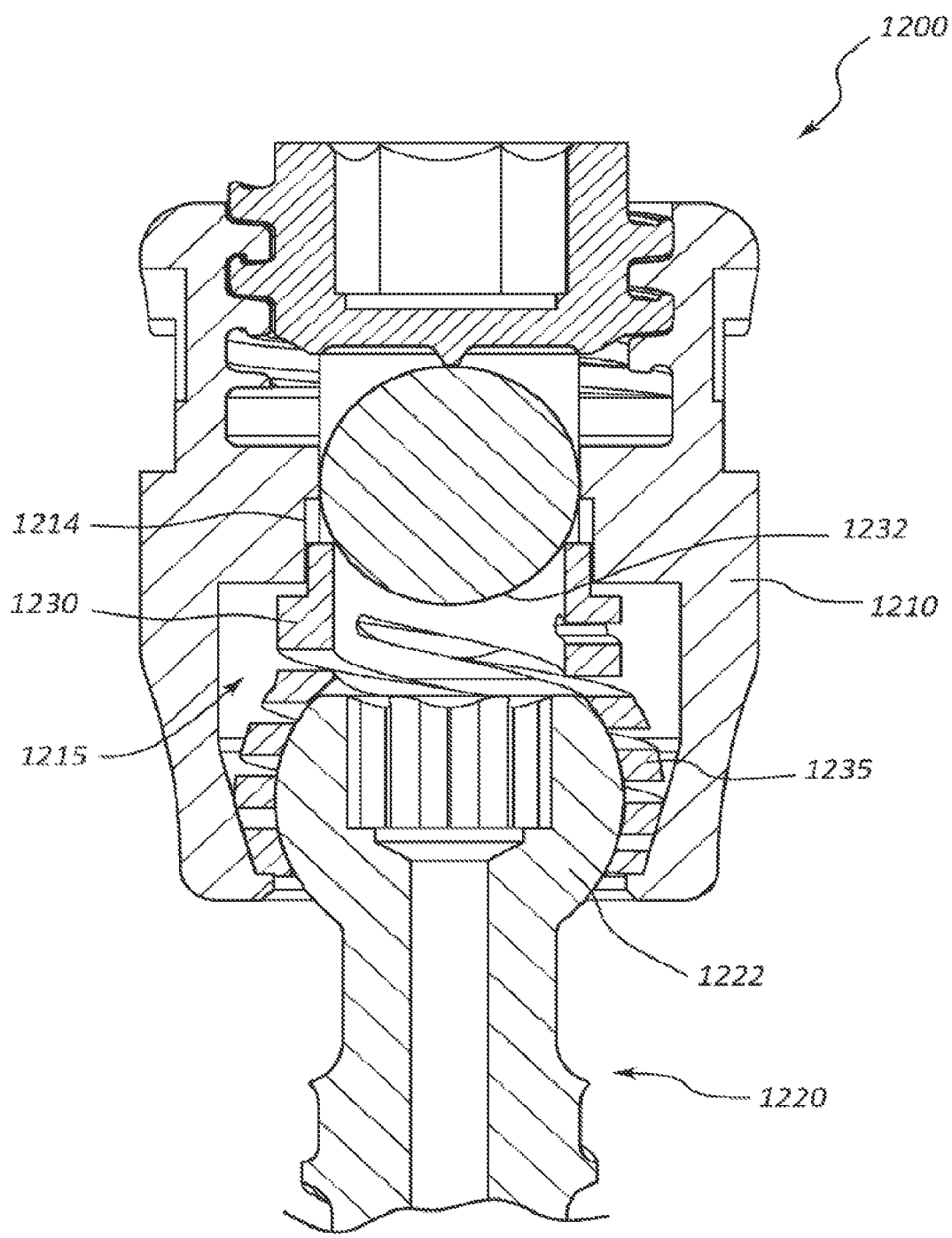
FIG. 12 is a cross-sectional view of a spinal fixation system according to still another embodiment shown after coupling a connector body of the system with a pedicle screw.
Figure 13:
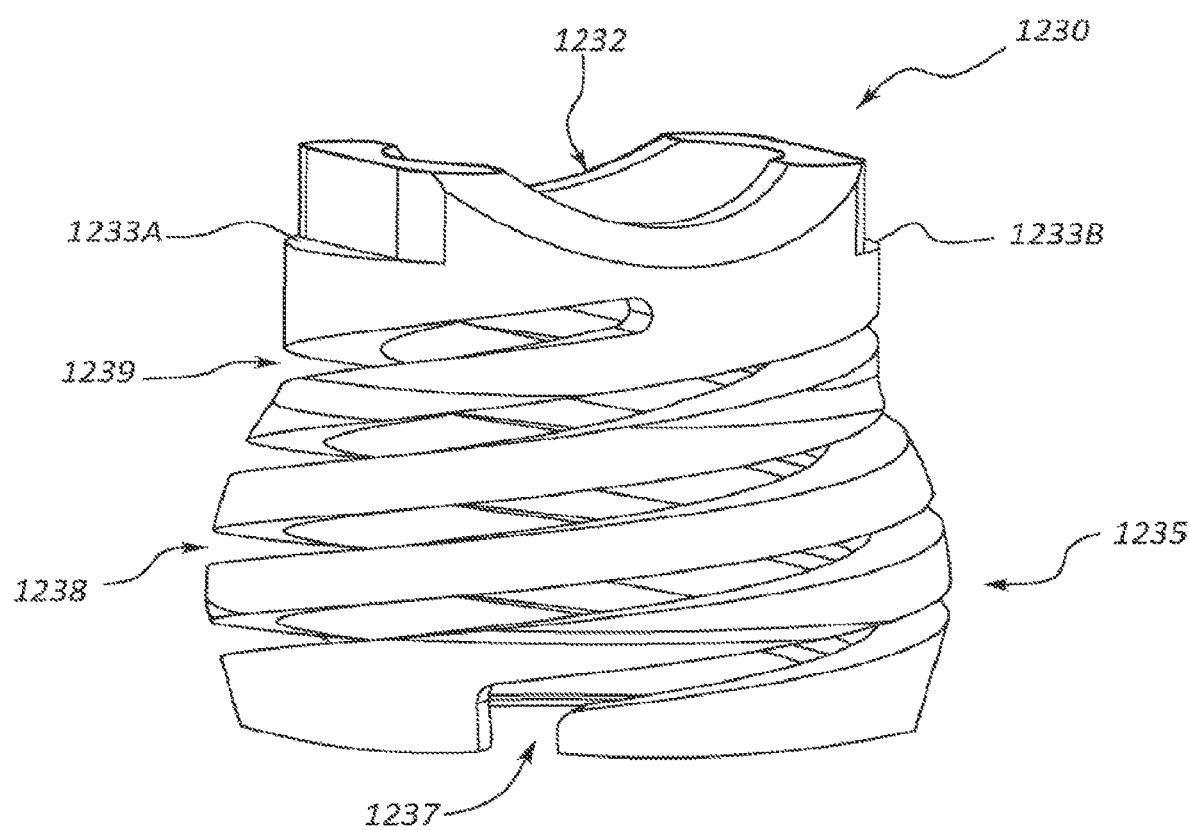
FIG. 13 is a perspective view of a spring cage structure element of the spinal fixation system depicted in FIG. 12.

FIGS. 12 and 13 illustrate yet another embodiment of a spinal fixation system 1200. Spinal fixation system 1200 is most similar to spinal fixation system 100 in that its spring cage structure 1230 comprises an integrated saddle 1232 but differs in several respects. For example, unlike spring cage structure 130, spring cage structure 1230 has three helical cuts, namely, first helical cut 1237, second helical cut 1238, and third helical cut 1239.

As previously described, each of the various helical cuts may begin and/or end at evenly-spaced locations along the periphery of spring cage structure 1230. In addition, each such cut may terminate at an open end at one end of the spring cage structure 1230 and terminate in a closed end near the opposite end of spring cage structure 1230, as best illustrated in FIG. 13. In addition, if desired, one or more of helical cuts 1237, 1238, and 1239 may terminate in an angled portion at its respective open end that extends from the helical portion to a straight cut extending at least approximately parallel to the axis of the spring cage structure 1230, as also illustrated in FIG. 13.

In addition, spring cage structure 1230 differs from spring cage structure 130 in that the spring portion 1235 containing the helical cuts 1237, 12381 and/or 1239 terminates in the seat portion 1232 of spring cage structure 1230. Further, although the exterior surface of spring portion 1235 is curved, such as spherically-shaped, the lower portion of spring portion 1235 comprises a straight taper that may be configured to engage with a corresponding tapered portion of chamber 1215 near the lower opening.

As previously described, the interior surface of spring portion 1235 may comprise a curved (in some embodiments spherical) surface configured to at least substantially match that of a corresponding exterior surface of a head 1222 of a bone screw 1220. As also previously described, spring cage structure 1230 further comprises opposing shelves 1233A and 1233B positioned on opposite ends of saddle portion 1232, which may be configured to engage corresponding features within connector body 1210, as shown in FIG. 12.

Finally, as also shown in FIG. 12, chamber 1215 comprises an upper narrowed region 1214 that accommodates the top of spring cage structure 1230 defining seat 1232 above shelves 1233A and 1233B, rather than accommodating the portion below shelves 133A and 133B as in system 100.

Figure 14:
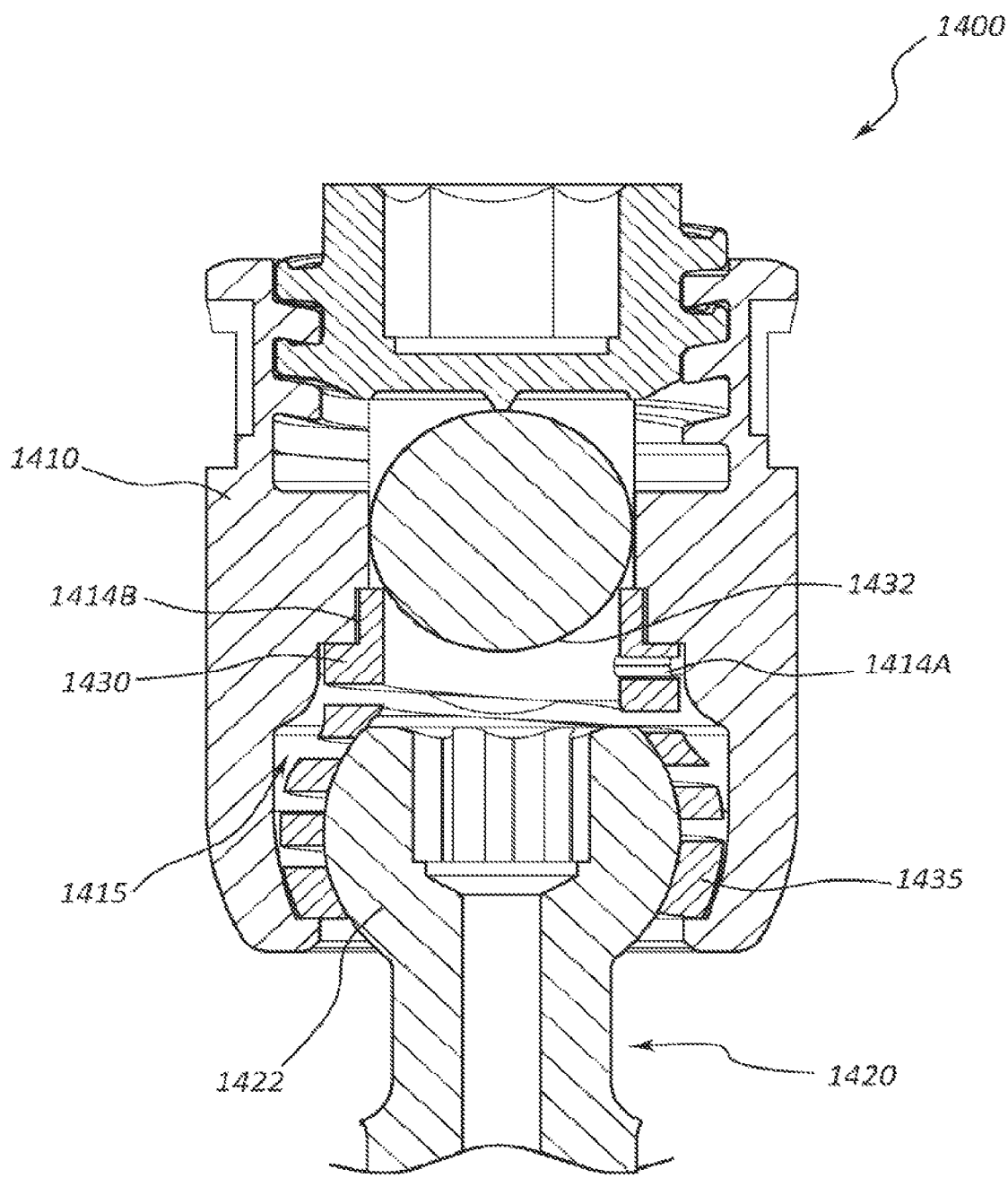
FIG. 14 is a cross-sectional view of a spinal fixation system according to yet another embodiment shown after coupling a connector body of the system with a pedicle screw.
Figure 15:
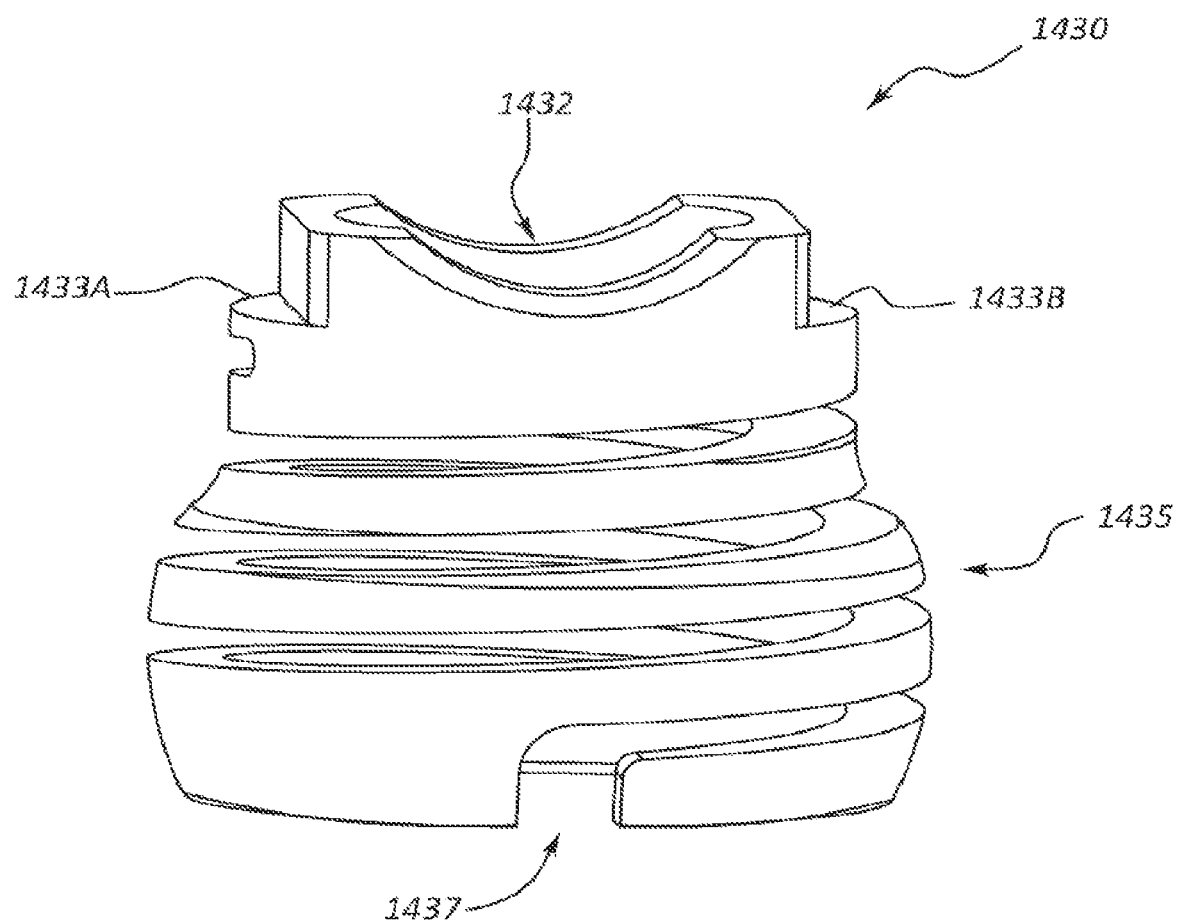
FIG. 15 is a perspective view of a spring cage structure element of the spinal fixation system depicted in FIG. 14.

FIGS. 14 and 15 illustrate still another embodiment of a spinal fixation system 1400. Spinal fixation system 1400, like system 1200, comprises a spring cage structure 1430 having an integrated saddle 1432 but differs in several other respects. For example, spring cage structure 1430 has only a single helical cut 1437. Further, the lower portion of spring portion 1435 of spring cage structure 1430 comprises a curved or rounded, rather than a straight taper that may be configured to engage with a corresponding curved lower portion of chamber 1415 near the lower opening.

As previously described, the interior surface of spring portion 1435 may comprise a curved (in some embodiments spherical) surface configured to at least substantially match that of a corresponding exterior surface of a head 1422 of a bone screw 1420. As also previously described, spring cage structure 1430 further comprises opposing shelves 1433A and 1433B positioned on opposite ends of saddle portion 1432, which may be configured to engage corresponding features within connector body 1410, as shown in FIG. 14.

Finally, as also shown in FIG. 14, chamber 1415 comprises two separate upper narrowed regions, namely a first upper narrowed region 1414A that accommodates the portion of spring cage structure 1430 below shelves 1433A and 1433B, and an adjacent second narrowed region 1414B above narrowed region 1414A that accommodates the narrowed top of spring cage structure 1430 defining seat 1432 above shelves 1433A and 1433B, as depicted in FIG. 14.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another, In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

I claim:

1. A spinal fixation system, comprising:
   a connector body configured to be coupled in a position relative to a spinal fixation rod; and
   a cage structure positioned within at least a portion of the connector body, the cage structure having a first end, a second end, a center line between the first end and the second end, and a sidewall between the first end and the second end and having a latitudinal circumference parallel to, and between, the first end and the second end, the first end having a first aperture to receive a head of an engagement member and the latitudinal circumference for aligning with a maximum diameter portion of the head of the engagement member, the sidewall having at least one helical sidewall aperture, the at least one helical sidewall aperture extending at least 360 degrees around the cage structure and traversing the center line and the latitudinal circumference, the second end including a surface for engagement with the spinal fixation rod;
   wherein the at least one helical sidewall aperture facilitates a first outermost circumference around the first end and a first distance between the first end and the second end, when the cage structure is in a relaxed position with the head of the engagement member disconnected from the cage structure;
   wherein the at least one helical sidewall aperture facilitates a second outermost circumference around the first end and a second distance between the first end and the second end, when the cage structure is in a compressed position from the head of the engagement member engaging the first end of the cage structure; and
   wherein the second outermost circumference is greater than the first outermost circumference; and
   wherein the first distance is greater than the second distance.

2. The spinal fixation system of claim 1:
   wherein the sidewall has a plurality of helical sidewall apertures; and
   wherein the plurality of helical sidewall apertures facilitate the first distance, the second distance, the first outermost circumference, and the second outermost circumference.

3. The spinal fixation system of claim 2 wherein at least one helical sidewall aperture in the plurality of helical sidewall apertures extends, in an axial dimension of the cage structure, at least one-half of a distance between the first end to the second end.

4. The spinal fixation system of claim 1 wherein the at least one helical sidewall aperture extends to at least one of the first end and the second end.

5. The spinal fixation system of claim 1 wherein each of the cage structure and the head of the engagement member comprises a frusto-spherical shape.

6. The spinal fixation system of claim 5, wherein a third outermost circumference exists around the first end once the head of the engagement member is engaged beyond the first end and within an interior of the cage structure; and
   wherein the third outermost circumference is less than the second outermost circumference.

7. The spinal fixation system of claim 1 wherein the surface of the second end comprises a saddle for engaging the spinal fixation rod.

8. The spinal fixation system of claim 7 wherein the saddle includes a slot for engaging an outer surface of the spinal fixation rod.

9. The spinal fixation system of claim 1 wherein the surface of the second end comprises a saddle for positioning relative to the spinal fixation rod.

10. The spinal fixation system of claim 9 wherein the saddle includes a slot for engaging an outer surface of the spinal fixation rod.

11. The spinal fixation system of claim 1 wherein the connector body comprises a chamber in which the cage structure is positioned.

12. The spinal fixation system of claim 1 wherein the sidewall has a total of three helical apertures, including the at least one helical sidewall aperture, and each of the three helical apertures traverses the center line.

13. The spinal fixation system of claim 1 wherein the cage structure has a third outermost circumference, greater than the first outermost circumference and the second outermost circumference, at a position between the first end and the second end.

14. An engagement structure positioned within a connector body of a spinal fixation apparatus, comprising:
   a first end for selectively flexing to expand in diameter when receiving a head of an engagement member, the engagement member for coupling to a portion of a spine; and
   a flexible sidewall between the first end and a second end, the flexible sidewall having a latitudinal circumference for aligning with a maximum diameter portion of the head of an engagement member and parallel to, and between, the first end and the second end, and a helical aperture extending at least 360 degrees around the spinal fixation apparatus and traversing the latitudinal circumference and a center line between the first end and the second end,
   wherein the helical aperture facilitates a first outermost circumference around the first end and a first distance between the first end and the second end, when the cage structure is in a relaxed position with the head of the engagement member disconnected from the cage structure;
   wherein the helical aperture facilitates a second outermost circumference around the first end and a second distance between the first end and the second end, when the cage structure is in a compressed position from the head of the engagement member engaging the first end of the cage structure; and
   wherein the second outermost circumference is greater than the first outermost circumference; and
   wherein the first distance is greater than the second distance.

15. The engagement structure of claim 14 wherein the helical aperture extends, in an axial dimension of the cage structure, at least one-half of a distance between the first end and the second end.

16. The engagement structure of claim 14 wherein a portion of the flexible sidewall, between the first end and the second end, has a greater circumference than a first circumference at the first end and greater than a second circumference at the second end.

17. A method of assembling a spinal fixation system, the method comprising:
   providing a connector body, the connector body configured to be coupled in a position relative to a spinal fixation rod;

providing a cage structure within an opening of the connector body, the cage structure having a first end, a second end, a center line between the first end and the second end, and a sidewall between the first end and the second end and having a latitudinal circumference parallel to, and between, the first end and the second end, the first end having a first aperture to receive a head of an engagement member and the latitudinal circumference for aligning with a maximum diameter portion of the head of the engagement member, the sidewall having at least one helical sidewall aperture extending at least 360 degrees around the cage structure and traversing the center line and the latitudinal circumference;

wherein the cage structure has a first outermost circumference around the first end and a first distance between the first end and the second end, when the cage structure is in a relaxed position with the head of the engagement member disconnected from the cage structure;

wherein the cage structure has a second outermost circumference around the first end and a second distance between the first end and the second end, when the cage structure is in a compressed position from the head of the engagement member engaging the first end of the cage structure; wherein the second outermost circumference is greater than the first outermost circumference;

wherein the first distance is greater than the second distance; and inserting the head of the engagement member into the cage structure of the connector body.

18. The method of claim 17, wherein the step of inserting the head of the engagement member into the cage structure of the connector body comprises compressing the first end of the cage structure with the engagement member to urge cage structure from the relaxed position to the compressed position such that the opening can receive and engage the head of the engagement member.

19. The method of claim 18, wherein, after the head of the engagement member is inserted into the cage structure the cage structure rebounds from the compressed position to the relaxed position.

20. The method of claim 19, wherein the head of the engagement member can rotate relative to the cage structure when the cage structure is in the relaxed position about the head of the engagement member.

* * * * *